United States Patent [19]
Zuckerman et al.

[11] Patent Number: 5,378,460
[45] Date of Patent: Jan. 3, 1995

[54] NEMATOCIDAL BACILLUS THURINGIENSIS BIOPESTICIDE

[75] Inventors: Bert M. Zuckerman, Amherst; M. Bess Dicklow, South Deerfield, both of Mass.; Nahum Marban-Mendoza, Turrialba, Costa Rica

[73] Assignee: Research Corporation Technologies, Tucson, Ariz.

[21] Appl. No.: 214,057

[22] Filed: Mar. 15, 1994

Related U.S. Application Data

[63] Continuation of Ser. No. 862,915, Apr. 3, 1992, abandoned.

[51] Int. Cl.[6] .................. A01N 63/00; A01N 25/00; C12N 1/20; C12P 1/04
[52] U.S. Cl. .................. 424/93.461; 424/405; 435/170; 435/252.31; 435/832
[58] Field of Search ............. 424/93 L, 405; 435/170, 435/252.31, 832

[56] References Cited

U.S. PATENT DOCUMENTS

| | | | |
|---|---|---|---|
| 4,948,734 | 8/1990 | Edwards et al. | 435/252.5 |
| 5,093,120 | 3/1992 | Edwards et al. | 424/93 |

FOREIGN PATENT DOCUMENTS

| | | |
|---|---|---|
| 0303426 | 2/1989 | European Pat. Off. . |
| 0352052 | 1/1990 | European Pat. Off. . |
| 0462721A2 | 12/1991 | European Pat. Off. . |

OTHER PUBLICATIONS

L. W. Bone, et al., (1988), *Journal of Invertebrate Pathology*, vol. 52, pp. 102–107, Factors Affecting the Larvicidal Activity of *Bacillus thuringiensis israelensis* Toxin for *Trichostrongylus colubriformis* (Nematoda).
L. W. Bone, et al, (1985), *Experimental Parasitology*, vol. 60 pp. 314–322, *Trichostrongylus colubriformis*: Egg Lethality due to *Bacillus thuringiensis* Crystal Toxin.
L. W. Bone, et al., (1989), *Journal of Invertebrate Pathology*, vol. 53, pp. 276–277, Acitivity of Commercial *Bacillus thruingiensis* Preparation against *Trichostrongylus colubriformis* and *Nippostrongylus brasiliensis*[1].
L. W. Bone, et al., (1987), *Journal of Nematology*, vol. 19(3), pp. 282–286, Changes is Morphology of *Trichostrongylus colubriformis* Eggs and Juveniles Caused by *Bacillus thuringiensis israelensis*[1].
R. Gaugler, et al., (1983), *Entomophaga*, vol. 28(4), pp. 309–315, Assessment of *Bacillus Thuringiensis* Serotype 14 and SteinernemaFeltiae (Nematoda:Steinernematidae) For Control of the Simulium Vectors of Onchocerciasis in Mexico.
J. R. Meadows, et al., (1989), *Invertebrate Reproduction and Development*, vol. 15:2, pp. 159–161, Lethality of *Bacillu Thuringiensis Morrisoni* for Eggs of *Trichostrongylus colubriformis* (Nematoda).
J. R. Meadows, et al., (1990), *Invertebrate Reproduction and Development*, vol. 17:1, pp. 73–76, *Bacillus thuringiensis* Strains Affect Population growth of the Free–Living Nematode Turbatrix Aceti.
G. Y. Osman, et al., (1988), *Anz. Schadlingskde., Pflanzenschutz, Umweltshutz*, vol. 61, pp. 35–37, Bio-efficacy of two insecticide strains of *Bacillus thuringiensis* as a biological control agent in comparison with a nematicide, Nemacur, on certain parasitic Nematoda.
K. P. Bottjer, et al., (1985), *Experimental Parasitology*, vol. 60, pp. 239–244, Nematoda: Suseptibility of the Egg to *Bacillus thuringiensis* Toxins.
D. A. Wharton, et al., (1989), *Invertebrate Reproduction and Development*, vol. 15:2, pp. 155–158, *Bacillus thuringiensis israelensis* toxin affects egg–shell ultrastructure of *Trichostrongylus colubriformis* (Nematoda).

*Primary Examiner*—Douglas W. Robinson
*Assistant Examiner*—Deborah K. Ware
*Attorney, Agent, or Firm*—Scully, Scott, Murphy & Presser

[57] ABSTRACT

The present invention relates to a newly discovered *Bacillus thuringiensis* strains and toxins which exhibits nematocidal activity in agricultural and horticultural settings. These strains and toxins can be used as a biocontrol agent in the treatment and prevention of nematode infection in plants, and particularly in commercially important crop plants.

17 Claims, No Drawings

NEMATOCIDAL BACILLUS THURINGIENSIS BIOPESTICIDE

This invention was made with Government support under HATCH 662 and NE 171 awarded by the U.S. Department of Agriculture. The Government has certain rights in the invention.

This is a continuation of copending application Ser. No. 07/862,915 filed on Apr. 3, 1992, now abandoned.

FIELD OF THE INVENTION

The present invention relates to novel *Bacillus thuringiensis* strains CR-371 and CR-450 which are nematocidal against soil and plant nematodes. These strains and the toxins produced thereby can be used as biocontrol agents in the treatment and prevention of nematode infection in plants and particularly in commercially important crop plants.

BACKGROUND OF THE INVENTION

Biopesticides are increasingly finding use in agricultural and horticultural settings for pest control. The potential benefit of biopesticides, especially relative to chemical pesticides, continues to spur the search for new biocontrol agents. For example, biopesticides create less pollution and environmental hazards than chemical pesticides. Further biopesticides appear to cause less problem with the development of drug resistance.

One significant agricultural pest amenable to control using biopesticides is the nematode. Nematode damage to crops is estimated to be more than $3 billion per year yet only about $180 million per year is spent in combating nematode diseases. Since chemical pesticide control of nematodes is relatively expensive, it is thus only used on high value crops. Effective biocontrol agents for nematodes, which are generally much cheaper to produce, thus promise to improve economic yield for a wider variety of crops.

*Bacillus thuringiensis* (Bt) strains are common insecticidal biocontrol agents, producing a polypeptide toxin which is deposited in crystalline inclusion bodies in the organism. However, the level of toxicity of both the Bt strains and the isolated toxin varies considerably, with some Bt strains failing to show insecticidal or other toxic activity (U.S. Pat. No. 4,948,734).

The effects of Bt as a nematocidal biocontrol agent have been investigated for free living nematodes, animal-parasitic nematodes, insect-parasitic nematodes and plant-parasitic nematodes. The strains *Bt israelensis, Bt kurstaki* and *Bt morrisoni* show considerable variability with respect to lethality for animal-parasitic and free living nematodes [Bottjer et al. (1985) Exp. Parasitol. 60: 239-244; Meadows et al. (1990) Invert. Reprod. Develop. 17: 73-76]. Similarly, two commercially available strains of Bt (SAN 415 and Dipel) show different toxicity effects as biocontrol agents for the plant-parasitic nematodes *Meloidogyne javanica* and *Tylenchulus semipenetrans* [Osman et al. (1988) Anz. Schädlingskde., Pflanzenschutz, Umweltschutz 61: 35-37].

While, Bt strains can be effective nematocidal agents, with the demonstrated variability in the Bt strains, there exists a need for additional Bt biopesticides to control the many nematodes that infect plants, especially economically important crop plants.

SUMMARY OF THE INVENTION

The present invention provides novel isolates of *Bacillus thuringiensis* (Bt) strains exhibiting nematocidal activity when applied to plants particularly to commercial crop plants, to the soil or to seeds of such plants. These isolates are Bt strains CR-371 and CR-450 and provide a means to control and prevent nematode diseases in plants. The two strains show differences in biological activity against root-knot nematode. Characterization by SDS gel electrophoresis showed important differences in the protein spectra displayed by CR-371 and CR-450. These strains are biopesticides and have many advantages relative to chemical pesticides, especially with respect to the environmental-effectiveness and cost-effectiveness. A method of using these strains to control or prevent nematode diseases in plants is also provided.

Another aspect of this invention relates to the toxins produced by the subject Bt strains and the use thereof in a method of controlling or preventing nematode diseases.

Yet another aspect of the present invention relates to a biological control agent which is a composition containing a nematocidally-effective amount of at least one of the subject strains with an agriculturally acceptable carrier.

DETAILED DESCRIPTION OF THE INVENTION

The present invention relates to newly discovered *Bacillus thuringensis* (Bt) strains and the spores thereof. These Bt strains are CR-371 and CR-450 which can be applied directly to seeds, plants or indirectly via the soil, and particularly to commercial crops, to reduce nematode diseases or to prevent nematode-induced crop destruction. These Bt strains are provided as pure cultures or formulated as biological control agents for treatment and prevention of nematode diseases. The Bt strains of the present invention have been isolated from nematode suppressly soils in Costa Rica, identified and characterized as new Bt strains. CR-371 and CR-450 are separable on the basis of their protein spectra, as demonstrated by SDS gel electrophoresis.

Bt is typically a motile, gram-positive microorganism which is a facultative anaerobe. The bacterium is rod-shaped and sporulates. Bt strains produce both endotoxins and exotoxins, with the former produced during sporulation and found deposited in the crystalline inclusion bodies of these microorganisms.

The Bt strains of the present invention were deposited on Jan. 10, 1992 in accordance with the Budapest Treaty with the American Type Culture Collection (ATCC), 12301 Parklawn Drive, Rockville, Md. 20852. The Bt strain CR-371 has been assigned ATCC accession number 55273 and the Bt strain CR-450 has been assigned ATCC accession number 55275.

The Bt strains CR-371 and CR-450 are nematocidal for soil and plant nematodes, including endoparasitic and free-living forms of plant-parasitic nematodes. Soil and plant nematodes include species selected from the genera Criconemella, Ditylenchus, Globodera, Helicotylenchus, Heterodera, Longidorus, Meloidogyne, Paratrichodorus, Pratylenchus, Radopholus, Rotelynchus, Rotylenchulus, Tylenchulus or Xiphinema. More particularly, the subject Bt strains are effective nematocidal agents against *Meloidogyne incognita, Meloidogyne javanica, Meloidogyne arenaria,*

*Meloidogyne hapla, Nacobbus abetrans, Pratylenchus penetrans, Pratylenchus brachyurus, Pratylenchus scribneri, Pratylenchus zeae, Ditylenchus dipsaci, Tylenchulus semipenetrans, Rotylenchulus reniformis, Radolpholus similis* and *Heterodera glycines*. More preferably, the subject Bt strains are effective nematocidal agents against *M. incognita, R. similis, P. penetrans, R. reniformis* and root-knot nematodes.

The subject Bt strains are neither phytotoxic nor pathogenic for plants. Phytotoxicity to plants by these biocontrol microbes has never been observed after more than 100 greenhouse trials. The assay for phytotoxicity included comparisons of root and top growth of plants treated in the greenhouse with these microbes as compared to untreated plants. Analyses included all trials with tomato and strawberry. Field studies on tomato, pepper, plantain and strawberry confirmed these observations. Therefore, none of these organisms are pathogenic to plants, as observed in any of the greenhouse or field trials.

The Bt strains of this invention can be grown in any conventional growth medium that supports Bacillus spp. For example, nutrient broth can be used or Bactopeptone broth supplemented with glucose and salts can be used. Hence, one suitable broth for Bt culture is composed of Bactopeptone 7.5 g/l, glucose 1.0 g/l, $KH_2PO_4$ 3.4 g/l, $K_2HPO_4$ 4.35 g/l, Salt solution 5.0 ml/l and $CaCl_2$ solution 5.0 ml/l. The Salt solution per 100 ml contains 2.46 g $MgSO_4 \cdot 7H_2O$, 0.04 g $MnSO_4 \cdot H_2O$, 0.28 g $ZnSO_4 \cdot 7H_2O$, and 0.40 g $FeSO_4 \cdot 7H_2O$. The $CaCl_2$ solution per 100 ml contains 3.66 g $CaCl_2 \cdot 2H_2O$, adjusted to pH 7.2. Any liquid or solid media which sup;ports growth of Bacillus spp., including media conditions which induce sporulation can be used to grow the subject Bt strains.

Typically, sterile media in a flask is inoculated with a Bt subculture and grown at 30° C. on a rotary shaker at 200 rpm until the desired culture density is achieved. The growth time varies with the desired culture density. Saturated cultures are usually obtained within 24 h of incubation. Culture density is monitored by conventional means, typically by measurement of the optical density of the culture. Viable cells are determined from the colony forming units obtained by plating serial dilutions of the culture on agar plates and counting the number of colonies which form. Alternatively, the subject Bt strains can be grown on solid agar media by streaking an inoculum across an agar plate with a sterilized wire loop, sterile toothpick or the like.

In addition, the growth procedures for Bt can readily be scaled up to large fermentors to produce large quantities of pure Bt cultures by methods well known in the art, i.e. batches of 50 to 250 liters or larger. Once grown, whether on large or small scale, the Bt strains can be concentrated by conventional means including centrifugation, filtration, sedimentation and the like.

In order to monitor the presence of these Bt strains on plants, seeds or in the field or soil, a marker gene can be introduced into the Bt strain by conventional means. Suitable marker genes include those genes which encode antibiotic resistance such as rifampicin. Markers can be introduced by plasmids, episomes, bacteria phages and the like and can integrate into the chromosome or reside independently in the cell.

Another aspect of the invention provides derivatives or mutants of Bt strains CR-371 and CR-450 which retain nematocidal activity but have other altered phenotypic or genotypic properties. Such mutants and derivatives can be made by genetic manipulations, either recombinant or classical techniques, which are well known in the art. For example, auxotrophies can be introduced by genetic recombination or screened for under appropriate media conditions. Likewise, phenotypic resistance to chemical or environmental conditions can be selected for using conventional genetic methods.

Another aspect of this invention is directed to a method of controlling or preventing nematode diseases in plants and particularly in commercial crops using Bt strain CR-371 or CR-450. To treat nematode diseases in accordance with the present method involves contacting the soil, the soil surrounding a plant, a plant, or seeds for a plant with a nematocidally-effective amount of at least one Bt strain selected from strain CR-371 or strain CR-450. Such treatments include pre-emergence or post-emergence treatment of the plant. In a preferred embodiment, the Bt strains can be applied singly or in combination. Similarly, the subject Bt strains can be applied as the vegetative cells, as spores or in combination.

As used herein "controlling or preventing" nematode diseases includes suppression of existing nematode populations in the soils or on plants as well as the prophylactic application of these Bt biopesticides to prevent nematode populations from becoming established in the soil or on the plants.

Plants which can be treated in accordance with this method include field crops, vegetables, ornamentals and fruit crops. Preferred commercial crops which can be treated to control or prevent nematode diseases include tomato, pepper, strawberry, oranges, pineapple, cotton, banana, plantain, coffee, soybean, potato, rice and fruit trees. All of these crops are susceptible to severe damage from nematode attack.

Among the nematode diseases treatable with the subject Bt strains are root-knot nematodes on vegetable and fruit trees; *Radopholus similis* on banana, plantain, pepper and citrus; *Heterodera glycines* on soybean, *Rotylenchulus reniformis* on many tropical and subtropical crops and *Pratylenchus penetrans* on an array of crops in the temperate zone. Hence, the present method can be used to control or prevent such nematode diseases caused in plants by plant-parasitic nematode species selected from the genera Criconemella, Ditylenchus, Globodera, Helicotylenchus, Heterodera, Longidorus, Meloidogyne, Paratrichodorus, Pratylenchus, Radolpholus, Rotelynchus, Rotylenchulus, Tylenchulus or Xiphinema. Particularly nematode species susceptible to treatment by this method include *M. incognita, M. javanica, M. arenaria, M. hapla, N. aberrans, P. penetrans, P. brachyurus, P. scribneri, P. zeae, D. dipsaci, T. semipenetrans, R. reniformis, R. similis* and *H. glycines*, and more particularly *M. incognita, P. penetrans, R. reniformis, R. similis, H. glycines* and root-knot nematodes.

The plants or crops are treated pre-emergence or Post-emergence with a nematocidally-effective amount of the Bt strains of the present invention. These strains are Bt CR-371 and CR-450 designated ATCC 55273 and 55275, respectively. Treatments include formulations having either or both the vegetative cells and the spores of these strains.

The term "nematocidally effective" amount is defined herein to be the population of the subject Bt strain inoculum required to reduce the pathological effects of the nematode pathogens and to obtain the desired population of the subject Bt strains in the soil and/or on the plant. The reduction of pathological effects can be measured by conventional means known in the art and can include such means as reduction of the number of nematodes per plant, increased crop yield, reduction of galling (e.g. as observed in pepper plants and tomatoes) and the like.

Treatment on a pre-emergence basis includes treatment of plant seeds from any time prior to implantation up to the appearance of a seedling or plantlet and includes such treatments as coating the seeds with a preparation containing one or more of the subject Bt strains. Pre-emergence treatment also includes application of the subject Bt strains such as by a drench, to the soil before planting seeds. Post-emergence treatment then encompasses treatment after the seedling or plantlet appears above the soil and includes treatments applied when the plants or plantlets are transplanted such as adding Bt drenches to the plant hole at transplantation, incorporating Bt into fertilizers or other preparations applied during transplantation or treatments applied during plant growth, such as with sprays, dusting, drenches and the like.

The present methods can be used with plants or crops grown in the greenhouse or in the field. An inoculum of one or more of the subject Bt strains is used such that colonization in the range of about $10^5$–$10^9$ colony forming units per gram (cfu/g) soil occurs and preferably about $10^5$–$10^8$ cfu/g soil. The inoculum can be applied directly to the seeds or plants, can be present in the soil before planting or can be distributed, e.g. by spreading, dusting of the like, over the crop or soil where the crop has been planted or is to be planted. Any inoculum of the subject Bt strains can be applied, provided that inoculum imparts a nematocidally-effective amount when treating nematode diseases.

Seeds can be treated by coating with a composition containing the subject Bt strains by dipping the seeds in a liquid or other composition containing these bacteria, by spraying the liquid on the seeds or applying the liquid to the seeds by any other conventional method known in the art for applying bacteria to seeds. These liquids can, in addition, contain methylcellulose.

A further aspect of this invention provides the subject Bt strains formulated as a biological control agent for control and prevention of nematode diseases in plants comprising a nematocidally-effective amount of at least one strain selected from strains CR-371 and CR-450 and an agriculturally acceptable carrier therefor. The biological control agent can be formulated with conventional agriculturally-acceptable carriers, such as those typically used with chemical pesticides. Any of the various types of compositions commonly used in applying chemical pesticides can be reformulated with a biopesticide in accordance with the present invention. Such compositions are well known in the art and provided, for example, by Lucas et al. (1985) *Introduction to Plant Diseases*, The AVI Publishing Company, Inc., Westport, Conn., especially Chapters 5-7. Such compositions include seed counts, fertilizers, peat, prepackaged soil, drenches, dusts, sprays, powders, liquids, mulch and the like.

When the biological control agent is formulated as peat, seed coat, fertilizer, prepackaged soil and the like, the Bt bacteria are grown in broth to the desired quantity, concentrated as necessary, and mixed with peat, seed coating or soil at the desired inoculum. Optionally this mixture may be cured by well known methods to form a granular composition.

The agriculturally acceptable carriers that can be used to disperse the subject strains on a pre- or post-emergence basis include all those commonly used carriers for dispersing nematocides on crops and plants. These carriers include water, clay, talc and other dusting agents. The subject Bt bacteria or spores in such compositions are present at a level of about $10^5$–$10^9$ cfu/g carrier, especially $10^5$–$10^8$ cfu/g carrier, and more especially $10^7$–$10^8$ cfu/g carrier, provided that the selected concentration is a nematocidally-effective amount for the composition in accordance with the present invention.

Any of the above biocontrol compositions, e.g. liquids, drenches, powders, peat, soil and the like can have nutrients and fertilizing agents included therein or an appropriate carrier medium such as water, oils or solid bases such as powders, peat, soil, fertilizer, clay, talc and any other dusting agent.

Another aspect of the present invention relates to the toxins produced by the subject Bt strains. These toxins are useful as nematocides for control and prevention of nematode diseases. The present Bt toxins include the endotoxins and exotoxins of the subject strains. The toxins are isolated from the cells, spores or the culture supernatants of stationary phase cells and used against the nematode species described herein.

In particular, the present invention provides a method of controlling or preventing nematode diseases which comprises contacting soil, seeds, or a plant susceptible to nematode infection with a nematocidally-effective amount of a toxin produced by *B. thuringiensis* strain CR-371, or *B. thuringiensis* strain CR-450. Suitable composition for application of Bt toxins are similar to those for application of the Bt strains. Hence, the liquids, trenches, fertilizers, peat, prepackaged soils, sprays, dusts, seed coats and the like can be formulated with the subject Bt toxins in a manner similar to formulations containing the subject Bt strains. The amount of Bt toxin provided in these formulations is a nematocidally-effective amount. For example, such amounts include formulations which provide at least about 10–50 g of toxin per acre.

In a further aspect of this invention, the genes for the subject Bt toxins can be isolated using recombinant DNA methodology. Once isolated, these genes can be inserted into other microorganisms to provide a toxin-delivery system. Alternatively, the genes can be engineered into plants to provide systemic immunity against endoparasitic nematiodes. The methodology for engineering plant cells is known [see, for example, Nester et al. (1984) *Ann. Rev. Plant Physiol.* 35: 387–399].

The following examples serve to further illustrate the invention.

EXAMPLE 1

The *B. thuringiensis* strains CR-371 and CR-450 were isolated from nematode suppressly soils obtained in Costa Rica in accordance with the methods described by Zuckerman et al. (1989) *J. Chem. Ecol.* 15: 1947-1955.

To evaluate protein content, *B. thuringiensis* isolates CR-371 and CR-450 were streaked onto Kings B (Difco-Pseudomonas Agar F) and incubated in the dark at 25° C. for 48 hours. Plates were flooded with Tris-HCl buffer, pH 6.8, and cells scraped off with a spatula. Bacterial cell suspensions were held at −80° C. for 24 hours then passed twice through a Kontes "mini-bomb" cell disruption chamber employing nitrogen at 100 kg/sq. cm. The homogenate was centrifuged at 11,000×g for 10 minutes and the supernatant retained. Protein concentration was determined with a BCA protein assay (Pierce) and treated for electrophoresis with SDS-mercap-toethanol. Proteins were separated by SDS gel electrophoresis on 7.5% polyacrylamide gels on a Hoefer Scientific SE600 vertical slab unit with discontinuous buffer, based on the method of Laemmli (1970) Nature 227: 680–685. Protein patterns of CR-371 and CR-450 differed markedly.

EXAMPLE 2

Four replicate plots (20'×10') containing two 20' rows of peppers were planted for each treatment for nematode biocontrol studies at the University of Puerto Rico Agricultural Research Station, Isabela, Puerto Rico, Summer, 1991. Each row contained 20 plants.

Pepper plantlets raised in a greenhouse were transplanted into the plot and treated with Bt CR-371, no added bacteria (control), or Nemacur (a commercial chemical nematocide) as indicated. For the Bt CR-371-treated plot, the plants were treated with a drench at the time of transplantation. The drench consisted of placing 50 ml of an overnight culture of Bt CR-371 around the root zone during transplantation. Plants in the control-treated plot, received 50 ml of nutrient broth without bacteria. Plants in the Nemacur-treated plot received amounts of nematocide as recommended.

The total area encompassed by this experiment was one acre. There were 5 pepper harvests. The yield data were combined arid are presented in Table 1.

The results showed significant increases in yield of pepper treated with CR-371, as compared to untreated plants (at the 5% level, analysis by Duncan's Multiple Range Test). Yield from the Nemacur treated plots were essentially the same as those treated with CR-371.

Samples for nematode populations were taken when the experiment was initiated, 6 weeks later and at the termination of the experiment. The results showed a 63% reduction in populations of the reniform nematode, *R. reniformis*, as compared to the untreated control. Analyses of gall indices at the end of the experiment showed a significant (5% level) reduction of galling (as compared to untreated plant. s) in plants treated with CR-371 (Table 1).

TABLE I

Pepper Yield & Gall Index From a Replicated Experiment in a Field Infested with Root-knot Nematode (*Meloidogyne incognita*), Isabela Exp. Station, Puerto Rico

| Treatment | Yield (kg)[1,2] | Gall Index[1] |
|---|---|---|
| Control | 11.4[a] | 2.04[c] |
| CR-371 | 19.7[b] | 1.21[d] |
| Nemacur | 19.4[b] | 0.45[e] |

[1]Figures followed by different letters are significantly different at the 5% level.
[2]Yields are given as the total kilograms (kg) pepper harvested from each treatment.

EXAMPLE 3

Four replicate plots (20'×10') containing 10 tomato or pepper plants per row were planted for each treatment for nematode biocontrol tests at the University of Puerto Rico Agricultural Research Station, Isabela, Puerto Rico, Fall, 1991.

The plants were treated as described in Example 2. The duration of the experiment was 3 months.

From these plots, peppers were harvested three times and tomatoes harvested five times. There were 4 applications of the biocontrol organism Bt CR-371, an untreated control or Nemacur in the amounts described above. The results are shown in Table 2 which provides the average yield for tomatoes and peppers as well as the percent yield over the control. Treatment with Bt CR-371 caused a 22% and a 3% yield increase for peppers and tomatoes, respectively, relative to the controls. However, it should be noted that the tomatoes were heavily affected by Pythium in this experiment.

Sampling for nematode populations and root-knot galling was as in Example 1. *R. reniformis* populations were 50% lower in the CR-371 plots as compared to untreated controls. CR-371 treatment resulted in a significant reduction in root galling due to *M. incognita* as compared to untreated controls.

TABLE 2

Yields of Pepper and Tomato From a Field Experiment, Isabela Exp. Station, Puerto Rico

| | Pepper[a] | | Tomato[a] | |
|---|---|---|---|---|
| Treatment | (Ave.Yield) Kg | Yield[b] % | (Ave.Yield) Kg | Yield[b] % |
| Control | 18.3 | — | 114.8 | — |
| CR-371 | 22.5 | 22 | 118.4 | 3 |
| Nemacur | 19.4 | 6 | 133.2 | 16 |

[a]Total Number of Plants: Tomato-1760; Pepper-880.
[b]Yield % is the increase in yield over the control.

EXAMPLE 4

In a field trial in Deerfield, Mass., strawberry plants treated with the CR-371 were compared with untreated control plants. There were 25 treated plants/plot, 5 replicates (total 125 plants) and the same number of untreated plants. Each of the treated plants had 50 ml CR-371 (1×10$^8$ bacteria/ml) applied at planting. The experiment was intitiated in June, 1990 and terminated one year later.

Plants treated with CR-371 had an average of 37% less *P. penetrans* (lesion nematodes) within roots as compared to controls at the conclusion of this experiment.

TABLE 3

Field Trial for Efficacy of Bt CR-371 in Reducing *P. penetrans* Infestation on Strawberry Plants

| Treatment | # berries/ meter | Mean wt. (g)/berry | # P.penetrans/ g root Fall 1990 | # P.penetrans/ g root Summer 1991 |
|---|---|---|---|---|
| None | 200.8 | 2.17 | 192.0 | 82.0 |
| CR-371 | 185.6 | 2.24 | 164.0 | 50.0 |

EXAMPLE 5

Greenhouse trials were conducted on tomato using the subject Bt strains. Controls received 2 applications of nutrient broth (50 ml). Infested controls received 2 applications of nutrient broth (50 ml) as well as 5000 *M. Incognita* second stage larvae/pot. Bt-treated plants received 2 applications of the indicated strain at 50 ml/pot (concentration 1×10$^{7\text{-}8}$ bacteria/ml). When both strains were tested, 2 applications of 25 ml of each strain were applied (1×10$^{7\text{-}8}$ bacteria/ml).

The results show a significant reduction of root-knot galling in plants treated with CR-371 (Table 4). There was no synergistic effect between the two strains when they were combined.

TABLE 4

Greenhouse Trial Comparing the Efficacy of Two Bt Strains Against Root-knot of Tomato

| Treatment[1] | dry weight shoots $\bar{x}$ | dry weight roots $\bar{x}$ | gall number[2] plant $\bar{x}$ | % Control |
|---|---|---|---|---|
| Control | 11.695 | 2.76 | — | — |
| Infested Control | 10.443 | 3.227 | 223.5$^a$ | — |
| CR-371/ M. incognita | 10.789 | 3.081 | 51.25$^b$ | 77.07 |
| CR-450/ M. incognita | 10.585 | 2.492 | 91.0$^{abx}$ | 59.29 |
| CR-371/CR-450/ M. incognita | 11.794 | 3.528 | 93.2$^{abx}$ | 58.3 |

[1] Each treatment was replicated five times.
[2] Figures followed by b are significantly different from the control at <5% level. Figures followed by x are significantly different from the infested control at <10% (not 5%).

We claim:

1. A method for controlling or preventing plant diseases caused by nematodes which comprises contacting soil, a plant, or a seed with a nematocidally-effective amount of a biologically pure culture of *B. thuringiensis* strain ATCC 55273 or mutants thereof, wherein said mutants exhibit nematocidal activity.

2. A biological control agent for control or prevention of nematocidal diseases in plants comprising a nematocidally-effective amount of a biologically pure culture of strain *B. thuringiensis* strain ATCC accession number 55273 or mutants thereof, wherein said mutants exhibit nematocidal activity and an agriculturally-acceptable carrier.

3. A biologically pure culture of *Bacillus thuringiensis* strain ATCC 55273 or mutants thereof, wherein said mutants exhibit nematocidal activity.

4. The method of claim 1 wherein said soil, plant or seed is contacted by coating said seed, drenching said soil, spraying said plant, dusting said plant or fertilizing said plant.

5. The method of claim 1 wherein said nematodes are selected from the genera consisting of Criconemella, Ditylenchus, Globodera, Helicotylenchus, Heterodera, Longidorus, Meloidogyne, Paratrichodorus, Pratylenchus, Radolpholus, Rotelynchus, Rotylenchulus, Tylenchulus and Xiphinema.

6. The method of claim 1 wherein said plant is a field crop plant, vegetable plant, ornamental plant or fruit crop plant.

7. The method of claim 6 wherein said plant is a tomato, pepper, strawberry, banana, coffee, soybean, orange, pineapple, potato, rice or cotton plant.

8. The method of claim 1 wherein said nematocidally-effective amount of said strain comprises about $10^3$ to about $10^8$ colony forming units per gram of a carrier.

9. The method of claim 1 wherein from about 8 to about 10 pounds of a composition comprising said strain and a carrier is applied per acre of crop area.

10. The method of claim 1 wherein said seed is a seed for a field crop plant, vegetable plant, ornamental plant or fruit crop plant.

11. The method of claim 10 wherein said seed is a seed for a tomato, pepper, strawberry, banana, coffee, soybean, orange, pineapple, potato, rice or cotton plant.

12. The method of claim 1 wherein controlling diseases caused by nematodes comprises suppression of existing nematode populations in the soil or on a plant.

13. The method of claim 9 wherein said carrier is water, oil, powder, peat, soil, fertilizer, clay or talc.

14. The biological control agent of claim 2 wherein said nematocidally effective amount of said strain comprises about $10^3$ to about $10^8$ colony forming units per gram of said carrier.

15. The biological control agent of claim 2 wherein said nematocidally-effective amount of said strain comprises about $10^6$ to about $10^8$ colony forming units per gram of said carrier.

16. The biological control agent of claim 2 wherein said nematocidally-effective amount of said strain is about $10^7$ to about $10^8$ colony forming units per gram of said carrier.

17. The biological control agent of claim 2 wherein said carrier is water, oil, powder, peat, soil, fertilizer, clay or talc.

* * * * *

UNITED STATES PATENT AND TRADEMARK OFFICE
CERTIFICATE OF CORRECTION

PATENT NO.   : 5,378,460
DATED        : January 3, 1995
INVENTOR(S)  : Bert M. Zuckerman, et al.

It is certified that error appears in the above-indentified patent and that said Letters Patent is hereby corrected as shown below:

On the Title Page, Section [56], under "OTHER PUBLICATIONS", Column 2, line 6: "SteinernemaFeltiae" should read --Steinernema Feltiae--

Column 3, line 33: "sup;ports" should read --supports--

Column 4, line 59: "Post-emergence" should read --post-emergence--

Column 6, line 66: "-were" should read --were--

Column 7, line 33: "arid" should read --and--

Column 7, line 46: "plant.s)" should read --plants)--

UNITED STATES PATENT AND TRADEMARK OFFICE
CERTIFICATE OF CORRECTION

PATENT NO. : 5,378,460
DATED : January 3, 1995
INVENTOR(S) : Bert M. Zuckerman, et al.

It is certified that error appears in the above-indentified patent and that said Letters Patent is hereby corrected as shown below:

Column 9, lines 29-30, claim 2, delete "accession number"

Signed and Sealed this

Twenty-sixth Day of March, 1996

*Attest:*

BRUCE LEHMAN

*Attesting Officer*   Commissioner of Patents and Trademarks